United States Patent [19]
Fisher

[11] Patent Number: 5,290,270
[45] Date of Patent: Mar. 1, 1994

[54] MEN'S UNDERGARMENT AND DISPOSABLE LINER FOR SAME

[76] Inventor: Warren G. Fisher, 3660 San Carlos Dr., St. James City, Fla. 33956

[21] Appl. No.: 98,749

[22] Filed: Jul. 28, 1993

Related U.S. Application Data

[63] Continuation of Ser. No. 847,576, Mar. 5, 1992, abandoned.

[51] Int. Cl.⁵ .................................................. A61F 13/15
[52] U.S. Cl. ..................................... 604/387; 604/389; 604/396; 604/397; 604/398; 604/399; 2/403
[58] Field of Search ............ 604/385.1, 389-391, 604/387, 394, 396-399; 2/401, 403, 406

[56] References Cited

U.S. PATENT DOCUMENTS

| | | | |
|---|---|---|---|
| 2,016,355 | 10/1935 | Alsop | 604/396 |
| 2,252,019 | 8/1941 | Meinecke et al. | 604/397 X |
| 3,088,462 | 5/1963 | Muto | 604/399 |
| 3,687,141 | 8/1972 | Matsuda | 604/397 X |
| 3,714,946 | 2/1973 | Rudes | 604/398 X |
| 4,338,939 | 7/1982 | Daville | 604/399 |
| 4,555,245 | 11/1985 | Armbruster | 604/396 |
| 5,098,422 | 3/1992 | Davis et al. | 604/385.1 |

FOREIGN PATENT DOCUMENTS

| | | | |
|---|---|---|---|
| 1516462 | 6/1969 | Fed. Rep. of Germany | 604/396 |
| 904058 | 8/1962 | United Kingdom | 2/406 |

Primary Examiner—Randall L. Green
Assistant Examiner—Mary Beth O. Jones
Attorney, Agent, or Firm—William E. Noonan

[57] ABSTRACT

A men's undergarment is disclosed. The undergarment includes a brief having front and rear sections, a crotch section interconnecting the front and rear sections and a pair of leg openings on respective sides of the crotch section. The front section and the crotch section include a relatively non-elastic region formed therein. An absorbent liner is provided for temporarily engaging inside surfaces of the front section and the crotch section. A pocket element is formed on the inside surface of the front section for releasably holding the liner generally in place when the front section is raised and lowered.

12 Claims, 2 Drawing Sheets

MEN'S UNDERGARMENT AND DISPOSABLE LINER FOR SAME

FIELD OF THE INVENTION

This application is a continuation of Ser. No. 847,576 filed Mar. 5, 1992, now abandoned.

This invention relates to a men's undergarment and, more particularly, to an undergarment that employs a disposable liner and a means for provisionally fastening the liner to the undergarment. This article is particularly suited for addressing minor urinary flow and leakage problems.

BACKGROUND OF THE INVENTION

With aging, many men experience relatively minor bladder leakage and urinary flow following urination. Although this problem does not rise to the level of incontinence, it is still very unpleasant and annoying. In particular, urinary leakage tends to stain and soil clothing and causes unpleasant odors and discomfort. To date, no undergarments or protective devices adequately address this difficulty. A variety of "adult diapers" and similar products are employed to battle incontinence. However, such devices are usually inappropriate for minor urinary leakage problems. They are typically fairly bulky and may be uncomfortable and/or unsightly. Moreover, the material used in large diaper-like devices is far more than is necessary to address the problem of minor urinary flow.

SUMMARY OF INVENTION

It is therefore an object of this invention to provide an improved men's undergarment that employs a disposable liner which reduces the staining, unpleasant odors, and discomfort that often accompany minor urinary leakage.

It is a further object of this invention to provide a men's undergarment with a disposable liner that stays securely in place as the undergarment is raised and lowered for urination.

It is a further object of this invention to provide a men's undergarment which, despite incorporating a disposable liner, is comfortable to wear and, at the same time, is not large, bulky or unsightly.

It is a further object of this invention to provide a disposable liner which may be quickly and conveniently applied to a men's undergarment and changed when required.

This invention results from a realization that minor urinary leakage problems experienced by men may be alleviated by utilizing a disposable liner that is secured to the front and crotch sections of a men's brief by structure constructed in the inside surface of the brief. This invention results from a further realization that such a liner may be held securely in place without shifting position, as the brief is lowered and raised for urination, by utilizing a non-resilient region within the front and crotch of the brief.

This invention features a men's undergarment including a brief having front and rear sections, a crotch section interconnecting the front and rear sections and a pair of leg openings on respective sides of the crotch section. The front section and the crotch section include a relatively non-elastic region formed therein. An absorbent liner temporarily engages the inside surfaces of the front section and the crotch section. There are means, connected to the inside surface of the front section, for releasably holding the liner generally in place when the front section is raised and lowered.

In a preferred embodiment, the front section and the crotch section include a relatively elastic fabric and the non-elastic region is defined by an elongate, non-elastic element that is secured to the inside surface of the elastic fabric. The liner may include a first portion for engaging the inside surface of the crotch section and a second portion for engaging the inside surface of the front section. Typically, the first portion of the liner is relatively broad and the second portion of the liner is relatively narrow.

The means for releasably holding may include a pocket element attached to the inside surface of the front section for removably receiving the second portion of the liner to hold the liner generally in place. The means for holding may further include an opening formed through the second portion of the liner and complementary first and second releasable fastening elements carried respectively by the pocket element and the inside surface of the front section. The fastening elements are aligned with and selectively interengaged through the opening in the second portion of the liner when the second portion of the liner is received in the pocket element. These fastening elements may comprise a snap fastener.

The non-elastic region may comprise an elongate strip that extends between the front section and the crotch section, and the pocket element is preferably attached to the front section proximate one end of the non-elastic strip. More particularly, the pocket element may extend transversely across the non-elastic strip and may include a resilient fabric. Adhesive means are carried by a bottom surface of the liner for releasably adhering the liner to the inside surfaces of the front section and crotch section of the brief.

DETAILED DESCRIPTION OF PREFERRED EMBODIMENT

Other objects, features and advantages will occur from the following description of a preferred embodiment and the accompanying drawings in which.

Figure 1:
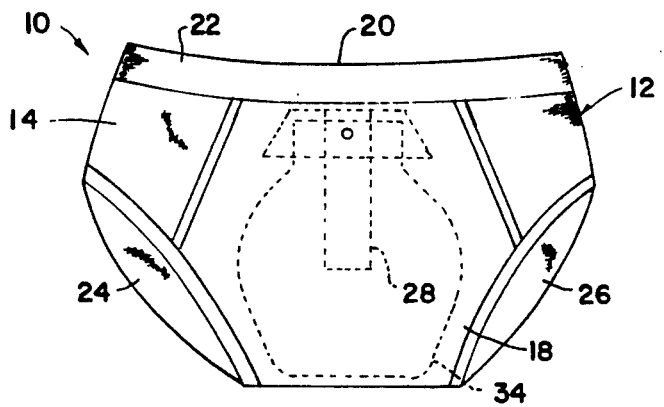
FIG. 1 is an elevational front view of a men's undergarment according to this invention.
Figure 2:
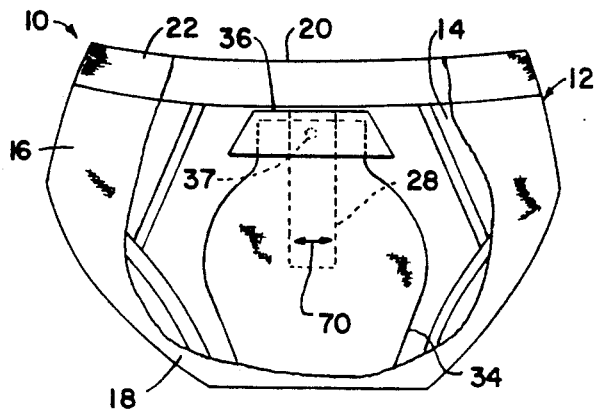
FIG. 2 is an elevational rear, cut away view of the men's undergarment of FIG. 1.

There is shown in FIGS. 1 and 2 a men's undergarment 10 that includes a brief 12 having a front section 14, FIG. 1, and a rear section 16, FIG. 2. A crotch section 18 interconnects the front and rear sections. Front section 14 and crotch section 18 do not include an accessing fly or other opening. Brief 12 further includes a conventional torso opening 20 that is surrounded by a waistband 22 and a pair of conventional leg openings 24 and 26 that are formed on respective sides of crotch section 18. The front, rear and crotch sections comprise a conventional elastic fabric, for example a cotton blend, such as is presently used in men's briefs. These sections may be integrally formed or secured together by stitching or other means. The openings, waistbands and other elements described above are constructed in any one of a number of manners known to those skilled in the art. Within the scope of this invention, the boundary between the crotch section and front and rear sections may vary and is not critical. The front and rear sections and crotch section are intended to refer to relative positions in the brief.

Figure 3:
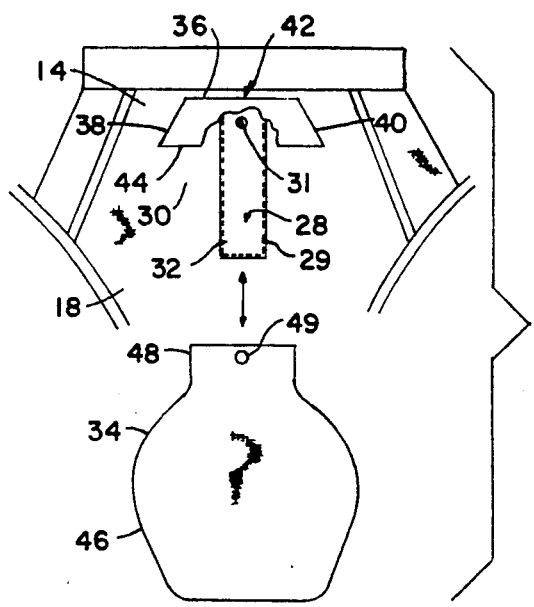
FIG. 3 is a perspective, generally top view of the disposable liner and the structure for temporarily holding the liner in the brief.

Front section 14 and crotch section 18 include a relatively non-elastic region 28 formed therein. More particularly, as best illustrated in FIGS. 2 and 3, region 28 includes an elongate, rectangular strip or element 29, FIG. 3, composed of material such as heavy cotton percale. Strip 29 is secured to the inside surface 30 of the resilient material that composes front section 14 and crotch section 18. Such attachment is made by suitable means such as stitching 32. Due to the non-elasticity of strip 29 the entire region 28 of front section 14 and crotch section 18, including the resilient material of the brief within that region, is effectively non-elastic. This provides significant advantages which are discussed more fully below. A conventional snap fastening element 31 is secured to the upper portion of non-elastic region 28 and is operably exposed from the inside surface of strip 29.

A disposable absorbent liner 34, FIGS. 2 and 3, is provisionally held within brief 12 such that it engages inside surface 30 of first section 14 and crotch section 18, as well as non-elastic strip 29. Means for releasably holding liner 34 in place within the brief include an elastic pocket element 36 that is secured to the inside surface of front section 14. Pocket 36 comprises a resilient material, which may be similar to that composing brief 10. Typically the pocket is somewhat thicker than the brief itself. The pocket element extends generally transversely across the upper end of non-elastic strip 29 and is secured to front section 14 along side edges 38 and 40 and a top edge 42, which is proximate the upper end of strip 29. A lower edge 44 of pocket element 36 is not connected to front section 14 and thereby defines an opening that generally faces crotch section 18. As best shown in FIG. 2, pocket 36 carries a second complementary snap fastening element 37 that is operably exposed within the pocket and is substantially aligned and operably engageable with snap fastening element 31. The operation of these elements will be described more fully below.

Figure 4:
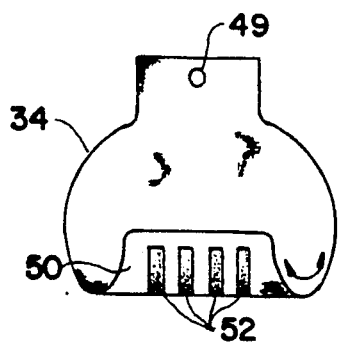
FIG. 4 is a perspective view of the liner and the adhesive means carried by its bottom surface.
Figure 5:
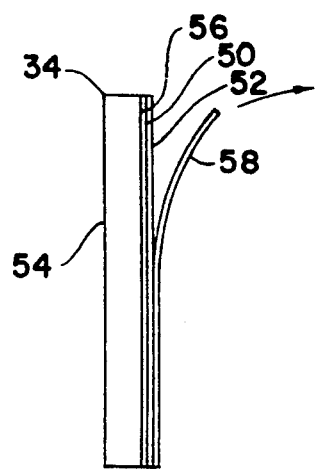
FIG. 5 is an elevational cross sectional view of the disposable liner material.

Absorbent liner 34 includes a relatively broad first portion 46 and a relatively narrow second portion 48 that extends generally forwardly from portion 46. An opening 49 is formed through the liner within portion 48. As shown in FIG. 4, liner 34 is highly flexible. Its bottom surface 50 is provided with adhesive strips 52 that permit the liner to releasably adhere to the brief. The adhesive is strong enough to generally hold liner 34 in place during normal wear but is readily releasable to permit removal and disposal when desired. The layered construction of liner 34 is shown more particularly in FIG. 5. Specifically, the liner includes an absorbent upper layer 54, which may include various absorbent materials such as cotton or cellulose and an intermediate moisture barrier 56, which may comprise materials such as polyethylene. Layer 56 defines the bottom surface 50 of the liner and adhesive strips 52 are applied thereto in a conventional manner. Before the liner is used, a removable plastic backing material 58 covers the adhesive.

Liner 34 is applied to brief 10 in the following manner. Brief 10 is set on a substantially flat surface with the snap elements separated and the pocket 36 open. Initially, backing 58 is removed from bottom 50 by peeling the backing away from adhesive 52 in the manner shown in FIG. 5. The liner is then introduced into the brief and portion 48 is inserted into pocket 36 until opening 49 aligns with snap fastening elements 31 and 37. The bottom surface 50 of liner 3 is engaged with the inside surface 30 of brief 10 and the liner is pressed against the brief and releasably adhered thereto by adhesive strips 52. Portion 48 of liner 34 fits snugly within pocket 36 and snap fastening elements 31 and 37 are connected through opening 49. As a result, the forward portion 48 of liner 34 is held securely in engagement with front section 14 of liner 34 and portion 46 extends to engage the crotch portion 18.

Figure 6:
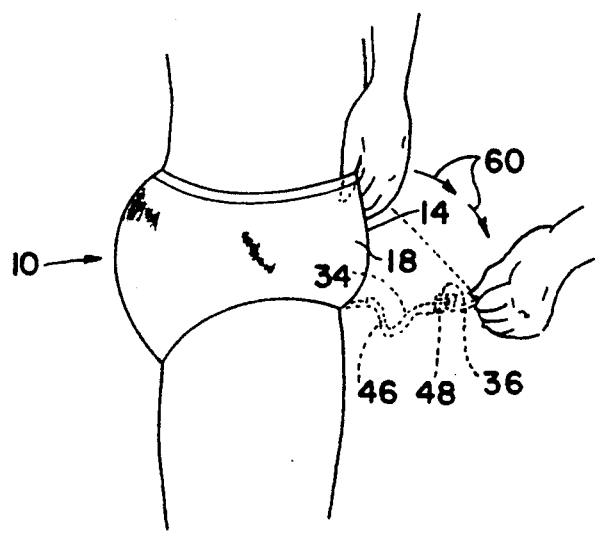
FIG. 6 is an elevational side view, partly in cross section and partly in phantom illustrating how the undergarment is raised and lowered for urination.

During use, liner 34 is held securely within the brief so that minor urinary leakage difficulties are overcome. Most significantly, the structure of this invention permits the liner to stay securely in place while and after the brief is lowered and raised for urination. As shown in FIG. 6, when the wearer desires to urinate he grasps the waistband in the front of the brief and lowers the front and crotch sections 14 and 18, as indicated in the directions of arrows 60, to the position shown in phantom. While the wearer urinates, the forward portion 48 of liner 34 is held securely in place by pocket 36 and the interengaged snap fasteners (not shown). Then, when the wearer finishes urinating and is tucking himself in, the pocket 38 and snap fasteners prevent the forward portion 48 of liner 3 from being pulled apart from the brief. Without such means of attachment the liner tends to separate from the brief. Additionally, the non-elastic region 28, shown in FIGS. 1–3, helps considerably to hold the liner in place as the brief is raised and lowered. Region 28 accomplishes this because it does not expand transversely as the brief is raised and lowered and therefore does not become loosened from the liner. Purely resilient brief material would tend to stretch laterally, as indicated by double-headed arrow 70 in FIG. 2. Such movement would likely cause the liner to separate from the brief. However, the use of non-elastic strip 29 and the resultant non-elastic region 28 eliminates this lateral movement and disruption of liner 34. As a result, brief 12 remains securely attached to the inside surface of the brief and in place, even as the front of the brief is raised and lowered. Because the liner remains in place, it is allowed to effectively accomplish its task of absorbing minor leakage that occurs following urination. Spotting of clothing and unpleasant odors and discomfort are therefore reduced significantly.

Typically, the liner is replaced following each use of the brief, or more frequently if desired. Replacement is performed very simply by separating fastening elements 31 and 37, removing forward portion 48 from pocket 36 and peeling the liner away from the brief. A new liner is then replaced in the manner described above. Although the embodiments described herein employ snap fastening elements, in alternative embodiments simply a pocket or other means may be utilized to hold the liner in place.

Although specific features of the invention are shown in some drawings and not others, this is for convenience only, as each feature may be combined with any or all of the other features in accordance with the invention.

Other embodiments will occur to those skilled in the art and are within the following claims.

What is claimed is:

1. A men's undergarment for managing urinary leakage, said undergarment comprising:

a men's brief having front and rear sections, a crotch section interconnecting said front and rear sections and a pair of leg openings on respective sides of said crotch section, said crotch section being further defined in its entirety by a part of said brief disposed between the wearer's thighs; said front section including an elastic fabric and a non-elastic region defined by an elongate, generally straight, non-elastic element that is secured to an inside surface of said elastic fabric and is located in said front section of said brief exclusively, entirely outside of said crotch section;

means for releasably holding an absorbent liner in temporary engagement with said non-elastic element, said means comprising;

a pocket element attached to an inside surface of said front section of said brief above said leg openings and being disposed across said non-elastic region; said pocket element having an opening that generally faces said crotch section;

said absorbent liner element directly and temporarily engaging said non-elastic region and having a portion that is removably received by said pocket elements for holding said liner generally in place when said front section is raised and lowered.

2. The undergarment of claim 1 in which said liner element includes a first portion for engaging said inside surface of said crotch section and a second portion for engaging said inside surface of said front section, and in which said pocket element removably receives said second portion of said liner to hold said liner generally in place.

3. The undergarment of claim 2 in which said means for holding further include an opening formed through said second portion of said liner and complementary first and second releasable fastening elements carried respectively by said pocket element and said inside surface of said front section, said fastening elements being aligned with and selectively interengaged through said opening in said second portion of said liner when said second portion of said liner is received in said pocket element.

4. The undergarment of claim 3 in which said fastening elements comprise a snap fastener.

5. The undergarment of claim 2 in which said non-elastic region comprises an elongate strip and in which said pocket element is attached to said front section proximate one end of said strip.

6. The undergarment of claim 5 in which said pocket element extends transversely across said non-elastic region.

7. The undergarment of claim 1 in which said pocket element includes a resilient fabric.

8. The undergarment of claim 2 in which said first portion of said liner is relatively broad and said second portion of said liner is relatively narrow.

9. A men's undergarment for managing urinary leakage, said undergarment comprising:

a men's brief having front and rear sections, a crotch section interconnecting said front and rear sections and a pair of leg openings on respective sides of said crotch section, said crotch section being further defined in its entirety by a part of said brief disposed between the wearer's thigh, said front section including an elastic fabric and a non-elastic region defined by an elongate, generally straight, non-elastic element that is secured to an inside surface of said elastic fabric and is located in said front section of said brief exclusively, entirely outside of said crotch section; and means connected to an inside surface of said front section above said leg openings and being disposed across said non-elastic element for releasably holding an absorbent liner in direct temporary engagement with said non-elastic region.

10. The undergarment of claim 9 in which said means for releasably holding include a pocket element attached to said inside surface of said front section for provisionally receiving at least a portion of said liner.

11. The undergarment of claim 10 in which said liner includes an opening formed therethrough and in which said means for releasably holding further include complementary first and second releasable fastening elements carried respectively by said pocket element and said inside surface of said front section, said fastening elements being aligned with and selectively interengaged through said opening in said liner when said liner is received in said pocket element.

12. A replaceable liner in combination with a men's undergarment, said undergarment including a brief that has front and rear sections, a crotch section interconnecting the front and rear sections, a pair of leg openings on respective sides of the crotch section, said crotch section being further defined in its entirety by a part of said brief disposed between the wearer's thighs, a generally straight, non-elastic region formed in its entirety in the front section, outside of said crotch section, and a pocket element attached to an inside surface of the front section above the leg openings and being disposed across the non-elastic region and having an opening that generally faces the crotch section, the liner comprising:

an absorbent first section provisionally engaging an inside surface of said crotch section;

an absorbent section portion that is removably received by said pocket element for holding said liner generally in place when said front section of men's brief is raised and lowered; and adhesive means carried by a bottom surface of said liner for temporarily adhering said liner to said inside surfaces of said front and crotch sections of said men's brief.

* * * * *